United States Patent [19]

Senda et al.

[11] Patent Number: 5,814,326
[45] Date of Patent: Sep. 29, 1998

[54] INSECT COMMUNICATION DISTURBING MATERIAL

[75] Inventors: Shuji Senda; Takeshi Saika, both of Osaka, Japan

[73] Assignee: Nitto Denko Corporation, Osaka, Japan

[21] Appl. No.: 553,100

[22] Filed: Nov. 3, 1995

[30] Foreign Application Priority Data

Nov. 4, 1994 [JP] Japan .................................. 6-270997
Nov. 4, 1994 [JP] Japan .................................. 6-270998

[51] Int. Cl.⁶ ............................................ A01N 25/34
[52] U.S. Cl. ........................ 424/411; 424/84; 424/405; 424/408
[58] Field of Search ................... 424/405, 408, 424/411, 84

[56] References Cited

U.S. PATENT DOCUMENTS

| | | | |
|---|---|---|---|
| 3,755,958 | 9/1973 | Bradshaw | 43/114 |
| 4,017,030 | 4/1977 | Coplan et al. | 239/44 |
| 4,317,836 | 3/1982 | Chuman et al. | 514/675 |
| 4,323,556 | 4/1982 | Moro et al. | 424/84 |
| 4,325,941 | 4/1982 | Moro et al. | 424/84 |
| 4,404,185 | 9/1983 | Maccone et al. | 424/84 |
| 4,671,010 | 6/1987 | Conlee et al. | 43/114 |
| 4,820,513 | 4/1989 | Howse | 424/84 |
| 4,925,730 | 5/1990 | Yamada et al. | 428/305.5 |
| 4,970,069 | 11/1990 | Kono et al. | 424/84 |
| 5,216,009 | 6/1993 | Fujimoto et al. | 514/406 |
| 5,308,613 | 5/1994 | Banfield | 424/84 |
| 5,359,808 | 11/1994 | Fitsakis | 43/132.1 |
| 5,484,599 | 1/1996 | Yoder et al. | 424/405 |
| 5,503,839 | 4/1996 | Saguchi et al. | 424/408 |
| 5,532,273 | 7/1996 | Ogawa et al. | 514/546 |
| 5,645,844 | 7/1997 | Henderson et al. | 424/405 |
| 5,690,951 | 11/1997 | Lew et al. | 424/410 |

FOREIGN PATENT DOCUMENTS

| | | |
|---|---|---|
| 0233109 | 8/1987 | European Pat. Off. . |
| 0256549 | 2/1988 | European Pat. Off. . |
| 0315994 | 5/1989 | European Pat. Off. . |

OTHER PUBLICATIONS

B.A. Leonhardt et al., "Effective Controlled–Release . . . Rate vs. Trap Catch", *Journal of Controlled Release,* vol. 1, 1984, pp. 137–141.

Chemical Patents Index, Documentation Abstracts Journal, Week 9229; 92–239896.

*Primary Examiner*—Robert H. Harrison
*Attorney, Agent, or Firm*—Sughrue, Mion, Zinn, Macpeak & Seas, PLLC

[57] ABSTRACT

An insect communication disturbing material comprises a covering material and a pheromone component to be included therein, wherein the included pheromone component exudes on the surface of the covering material in such a condition that it can be transferred and adhered to insect pests which contact with the insect communication disturbing material. The material is used in a method for disturbing insect communication which comprises attracting male adult insects to the above-described material, thereby effecting their contact with the insect communication disturbing material and adhesion of the pheromone component to the body of the male adults, and subsequently allowing the contacted males to be free without capturing them.

6 Claims, No Drawings

ન,814,326

INSECT COMMUNICATION DISTURBING MATERIAL

FIELD OF THE INVENTION

This invention relates to an insect communication disturbing material for use in insect pest control and to a method for disturbing insect communication using the material, more particularly to an insect communication disturbing material for use in of a novel insect communication disturbing method which is entirely different from the prior art methods and to a method for disturbing insect communication using the material.

BACKGROUND OF THE INVENTION

In comparison with the conventionally used application of insecticides, pheromone-aided insect pest control methods hardly exert influences upon beneficial animals as natural enemies of pests, as well as other animals including humans, and do not show residual toxicity against crops. Also, insecticidal activities of insecticides are reduced in many cases when they are used repeatedly due to the emergence of drug-resistant insects, but the pheromone-aided methods do not cause such emergence of resistant insects and therefore are markedly safe and useful.

Under such circumstances, pheromone components of various insect pests have been studied, and a number of pheromone components have recently been isolated from natural resources and identified.

With regard to the mode of pest control so far proposed, a pheromone component is packed in microcapsule or contained in gum arabic, dextrin or the like supporting carrier by means of impregnation or inclusion, with such a design that the pheromone component is vaporized gradually into the air to disturb communication between male and female insects. Some of such pheromone-aided communication disturbing materials have been put into practical use for the control of tea insect pests and the like.

In these prior art controlling methods effected by the use of insect communication disturbing materials, opportunity for male and female insect pests to perform copulation is reduced by a process in which a compound similar to a pheromone component released by female adults of interest is vaporized in advance in an area where the insect is to be controlled so that male adults cannot find exact positions where female adults are present or by a process in which an element of the pheromoneconstituting component is vaporized in a large quantity in order to change apparent composition ratio of the pheromone released by the female adults.

However, a large quantity of pheromone is required when insect pest control is carried out in a broad area by the prior art insect communication disturbing method, because it is necessary to vaporize the pheromone in a high concentration within all activity ranges of the insect pest to be controlled by arranging a large amount of a pheromone preparation (insect communication disturbing material) in the area. Especially, when insect pests which inhabit relatively high places or roadside trees and the like plants lined up in a single file are to be controlled, it is difficult to keep the pheromone as a high concentration atmosphere so that high cost cannot be avoided.

As has been described above, the commonly used insect communication disturbing methods can be used only within limited areas, are costly and require time and labor. Because of this, great concern has been directed toward the development of an insect communication disturbing material which can be applied to a novel insect pest controlling method that can overcome these problems involved in the prior art.

SUMMARY OF THE INVENTION

An object of the present invention is to provide a novel insect communication disturbing material and to an economical and efficient method for disturbing insect communication using the material.

Taking the above-described situation into consideration, the inventors of the present invention have conducted intensive studies on the development of a novel insect communication disturbing method and found that, unlike the case of the prior art communication disturbing method in which a pheromone component is vaporized and released from an insect communication disturbing material to create a pheromone atmosphere in the controlling area, opportunity for performing copulation by insect pests themselves can be inhibited when male adults are made into mimic female insects by disguising them as females through the adhesion of a pheromone to male adults attracted by and contacted with a insect communication disturbing material, and a secondary communication disturbing action can be generated when the male adults thus made into mimic females are allowed to fly freely without capturing them to create communication disturbance among other male adults. The present invention has been accomplished on the basis of this finding.

The present invention provides an insect communication disturbing material which comprises a covering material and a pheromone component to be included therein, wherein the included pheromone component exudes on the surface of the covering material in such a condition that it can be transferred and adhered to insect pests which contact with the insect communication disturbing material.

The present invention also provides a method for disturbing insect communication which comprises attracting male adult insects to the above-described insect communication disturbing material, thereby effecting their contact with the insect communication disturbing material and adhesion of the pheromone component to the body of the male adults, and subsequently allowing the contacted males to be free without capturing them.

DETAILED DESCRIPTION OF THE INVENTION

The term "pheromone component" used herein includes one or more components of pheromone and substances analogous to pheromone, which are capable of exerting the effect of the present invention, as well as intact pheromone. There have been numerous reports of pheromones and the pheromone component to be used in the present invention can be synthesized by the known method described therein. Alternatively, commercially available pheromone product can be used.

The pheromone component to be used in the insect communication disturbing material of the present invention is not particularly limited, and any insect pest pheromone may be used. Illustrative examples of such insect pests include *Chilo suppressalis, Plodenia litura, Laphygma exigua, Plutella maculipennis, Acrolepia alliella, Agrotis fucosa, Adoxophyes fasciata, Homona magnanima, Caloptilia theivora, Dichocrocis punctiferalis, Grapholita molesta, Adoxophyes orana, Archips breviplicanus, Synanthedon hector, Lyonetia clerkella, Lithocolletis ringoniella, blugrass webworm* (*Parapediasia teterrella* (*Zincken*)),

*Rusidrina depravata, Anomala rufocuprea, Popillia japonica, Cylas formicarius, Anomala cuprea, Anomala albopilosa, Anomala octiescostata* (*Burmeister*), *Hyphantria cunea, Lymantria dispar* and the like. As the type of pheromone, sex pheromone is preferred.

Examples of the covering material to be used for the inclusion of the pheromone component include plastic resins such as polyolefin, polysulfone, polyester, ethylene/vinyl acetate copolymer, polyamide, polystyrene, poly(meth) acrylate and the like resins. Of these, polyester resin is desirable as a material by which transfer rate of the pheromone component to the covering material surface can be easily controlled.

Though not particularly limited, the covering material may have at least one shape selected from a sheet form, a capsular form, a tubular form and a hollow fiber membrane. Such shapes are desirable, because the pheromone component exudes from the covering material gradually and the effect of the present invention therefore can be fully exerted. Of these shapes, the sheet-like form is particularly preferred, because larger surface area of the covering material leads to higher efficiency in transferring and adhering the exuded pheromone to insect pests, in addition to its easy handling.

When the covering material has a sheet-like shape, it may be prepared preferably from the above-described polyester resin in view of its mechanical strength and weatherability and controllability of transfer rate of the pheromone component (release rate and transfer rate can be easily adjusted to be constant). Also, since the pheromone component included in the covering material gradually exudes by its diffusion transfer onto the surface under the influence of density gradient, type of the covering material and the like, its persistent effect can be obtained for a prolonged period of time by controlling its diffusion transfer rate. In the case of a covering material made of a plastic material, the diffusion transfer rate can be changed by adjusting glass transition temperature (Tg) of the plastic material, so that the use of two or more polyester resins having different glass transition temperatures makes it easy to control the glass transition temperature and therefore the diffusion transfer rate of the pheromone component. As the glass transition temperature is raised, the diffusion transfer rate of the pheromone component included in the covering material becomes higher. On the other hand, as the glass transition temperature is lowered, the diffusion of the pheromone component is suppressed. The glass transition temperature preferably ranges from $-50°$ to $100°$ C.

Inclusion of the above-described pheromone component into a covering material can be effected by a method in which the covering material and the pheromone component are mixed at an optional ratio in the presence of an organic solvent and the mixture is formed into a desired shape or by a method in which the covering material is formed into a desired shape in advance and then the pheromone component is included therein by impregnation, injection or the like means. In this instance, the organic solvent to be used includes toluene, acetone, ether, dichloromethane, methyl ethyl ketone and the like. The mixing ratio of the covering material to the pheromone component is preferably 1:1 to 1:100 by weight. When the film-like insect communication disturbing material is formed, the mixture of the covering material, the pheromone component and the solvent can be spread in the form of film and dried at a temperature of from room temperature to $150°$ C.

According to the insect communication disturbing method of the present invention, male adult insects are firstly attracted to and contacted with an insect communication disturbing material which includes the above-described pheromone component. In that case, a pheromone stock solution may be used as the pheromone component directly or in the form of a sustained release preparation well known in the art. In the most simple form, the pheromone stock solution is put in a container of optional shape having an opening on its upper part, or it is allowed to penetrate into the inside of cotton, non-woven fabric, rubber, a porous polymer sheet, a hollow fiber membrane or the like so as to allow the pheromone to adhere to male adult insects.

The following describes an example of the method for the preparation of a sheet-like insect communication disturbing material.

To 100 weight parts of a polyester resin are added 1 to 100 weight parts of the pheromone component of insect pest to be controlled and optional components such as an antioxidant, a light stabilizer and the like as occasion demands. After the mixture is uniformly dissolved in the presence of an organic solvent, the resulting solution is coated on one side or both sides of a plastic sheet to be used as the supporting material and then dried to obtain the insect communication disturbing material of the present invention.

The supporting material may be made of polyester, polypropylene, polyethylene or aluminum laminate film in the sheet-like or plate-like form having a thickness of from 10 $\mu$m to 2 mm.

The coating can be effected by the method of immersing the supporting material in the pheromone mixture, the method of applying the pheromone mixture on one side of the supporting material using a brush or a roll, or the method of extruding the mixture through a split to spread it on the supporting material. This procedure is generally carried out at a temperature of from room temperature to a boiling point of the solvent. Then, the material is dried at a temperature of, for example, from room temperature to $150°$ C. The thus-dried material has a thickness of from 10 to 200 $\mu$m, preferably 30 to 100 $\mu$m.

When a peeling-treated plastic sheet, so-called separator, is used as the supporting material, the sheet-like insect communication disturbing material is peeled off from the supporting material after coating and drying of the solution to give an insect communication disturbing material which exudes the pheromone component from the entire sheet area (both sides).

Also, when using as the supporting material a plastic sheet which is not peeling-treated and a material which has excellent affinity (adhesive property) for the covering material, such as a polyester sheet, and is impermeable to the pheromone component, one side of the resulting sheet-like insect communication disturbing material is covered with the supporting material and an insect communication disturbing material in which the pheromone component exudes from only one side is obtained. Since such a mode of insect communication disturbing material is excellent in exerting sustained release effect and has a non-exuding surface side, it does not cause adhesion of the exuded pheromone component to the hand and the like at the time of its handling and can be easily handled when it is applied to roadside trees and the like for example by directly fixing it with a pressure sensitive adhesive double coated tape or by fixing it to a board or a commercially available capturing apparatus.

A covering material sheet is formed on one side of a supporting material as described above. It is not always necessary to make such a sheet into a porous body of open cell system in order to effect exudation of the pheromone component, and a non-porous sheet may also be used provided that its material can perform so-called blooming, a phenomenon that the pheromone component is dissolved and transferred by diffusion to the material surface via density gradient and the like.

According to the thus obtained insect communication disturbing material of the present invention, the pheromone component included therein exudes on the surface of the covering material to form an ultra-thin layer of about 0.1 to 10 μm in thickness. The thus exuded pheromone component vaporizes gradually in the air and attracts male adults of the insect pest of interest to cause their contact with the insect communication disturbing material of the present invention. As the result, the exuded pheromone component is transferred and adhered to the thus contacted male adults which then fly away from the insect communication disturbing material.

According to the insect communication disturbing method of the present invention, male adults attracted by the pheromone component in the above-described manner contact with the pheromone component which is subsequently transferred and adhered to their bodies. The method of the present invention is characterized in that the thus attracted male adults are not captured but allowed to be free. That is, though the pheromone-adhered male adults fly about in the field, they cannot detect the original pheromone component generated by female adults because of the adhered pheromone component, so that the male adults miss the opportunity of performing copulation, or the female adults cannot lay eggs. In this way, emergence of the next generation insect pests can be inhibited. In addition, since the male adults thus contacted with the pheromone component are not captured but allowed to be free, they fly about in their habitat vaporizing the pheromone component in the air, so that they become a female-mimicked secondary pheromone generating source and attract other male adults. As the result, these male adults attracted by the female-mimicked male adults also miss their opportunity to perform copulation, thus expanding the insect communication disturbing effect over a broad range.

The material of the present invention can be placed so as to give a pheromone concentration of from 0.01 g/10 ares to 100 g/10 ares at upper places within activity ranges of the insect pest to be controlled, though it varies depending on sensitivity of the insect to the pheromone.

The present invention can exert its insect communication disturbing effect over a broad range of insect habitation, because not only the communication of male insect pests (adults) attracted by the vaporized pheromone component is disturbed but also the thus attracted insect pests are positively used as the source of pheromone. In consequence, it renders possible disturbance of insect communication in the area of roadside trees and tall plants, which cannot be achieved easily by the prior art means.

Particularly, the insect communication disturbing material and insect communication disturbing method of the present invention are markedly useful against insect pests which have relatively short copulation time and period and narrow habitation range. For example, a fall webworm, *Hyphantria cunea*, is an insect pest which can be controlled by the present invention effectively, because its copulation time is 10 to 15 minutes per day, its copulation period is about 1 week per 1 generation and its habitat is roughly limited to roadside trees or a row of trees such as of plane trees, cherry trees and the like.

Examples of the present invention are given below by way of illustration but not by way of limitation, because various applications can be made therefrom within the technical idea of the present invention.

EXAMPLE 1

A 24 mg portion of a polyester resin (glass transition temperature, 47° C.) and 12 mg of another polyester resin (glass transition temperature, 60° C.) were dissolved in 30 mg of methyl ethyl ketone, and 6 mg of *Hyphantria cunea* pheromone was added to the resulting solution and uniformly dissolved.

The thus obtained solution was coated and dried on a polyester film having a thickness of 75 μm in such an amount that thickness of the coated layer after drying became 50 μm, thereby preparing an insect communication disturbing material of the present invention having a supporting material on one side.

EXAMPLE 2

A 12 mg portion of a polyester resin (glass transition temperature, 47° C.) and 12 mg of another polyester resin (glass transition temperature, 60° C.) were dissolved in 30 mg of methyl ethyl ketone, and 6 mg of *Hyphantria cunea* pheromone was added to the resulting solution and uniformly dissolved.

The thus obtained solution was coated and dried on a polyester film having a thickness of 75 μm in such an amount that thickness of the coated layer after drying became 50 μm, thereby preparing an insect communication disturbing material of the present invention having a supporting material on one side.

EXAMPLE 3

A polyester cap made of the polyester resin used in Example 2 was impregnated with 10 mg of *Hyphantria cunea* pheromone and allowed to stand for 24 hours, thereby preparing an insect communication disturbing material of the present invention in which the pheromone component exudes from the surface of the polyester cap.

EXAMPLE 4

A 30 mg portion of a polyester resin (melting point, 170° to 180° C.) was dissolved in 150 mg of dichloromethane, and 10 mg of *Lymantria dispar* pheromone was added to the resulting solution and uniformly dissolved.

The thus obtained solution was coated and dried on a polyester film having a thickness of 75 μm in such an amount that thickness of the coated layer after drying became 50 μm, the resulting material was cut into a size of 1 cm×1 cm and then the polyester film was peeled off, thereby preparing an insect communication disturbing material of the present invention in which the pheromone component exudes from both sides.

TEST EXAMPLE 1

The insect communication disturbing material of the present invention prepared in Example 1 was cut into such a size that its coated area became 2 cm×2 cm and attached to a 1.5 m high branch of a plane tree to observe the behavior of *Hyphantria cunea* attracted thereby. Its male adults attracted by and contacted with the preparation of the present invention and immediately departed therefrom. They were not attracted again during the action time of the day. In addition, other male adults were observed which approached the *Hyphantria cunea* males that had contacted with the insect communication disturbing material of the present invention, attracted by the contacted males.

TEST EXAMPLE 2

The insect communication disturbing material of the present invention prepared in Example 1 was cut into such a size that its coated area became 2 cm×2 cm, and a total of 11 of the thus prepared pieces were arranged in 27 roadside trees (plane trees) in Himeji-shi, Hyogo, Japan. The arrangement was carried out on July 15 before the time of the emergence of adults, and the average number of nest webs of the next generation larvae (the number of nest webs (egg clusters) per one tree) was examined on August 12 after the emergence of adults. As a comparison, a non-treated plot was arranged and examined in the same manner.

As the result, the average number of nest webs was 1.21 in the non-treated plot and 0.62 in the treated plot where the insect communication disturbing material of the present invention was arranged, thus confirming its significant insect communication disturbing effect.

TEST EXAMPLE 3

The insect communication disturbing material of the present invention prepared in Example 2 was cut into such a size that its coated area became 2 cm×2 cm, and the thus cut pieces were arranged on every other of 25 roadside trees (plane trees) in Sumida-ku, Tokyo, Japan. The arrangement was carried out three times on May 12, July 8 and August 20 before the emergence of adults, and the average number of nest webs of the next generation larvae was examined on June 15, August 19 and October 15 after respective emergences of adults. As a comparison, a non-treated plot was arranged and examined in the same manner.

As the result, average numbers of nest webs were 1.24 (first time), 1.54 (second time) and 0.25 (third time) in the non-treated plot and 1.09 (first time), 0.60 (second time) and 0 (third time) in the treated plot where the insect communication disturbing material of the present invention was arranged, thus confirming that its insect communication disturbing effect becomes significant by its repeated arrangement.

EXAMPLE 5

A 18 mg portion of a polyester resin was dissolved in 30 mg of methyl ethyl ketone, and about 6 mg of *Hyphantria cunea* pheromone was added to the resulting solution and uniformly dissolved.

The thus obtained solution was coated on a polyester film having a thickness of 75 $\mu$m in such an amount that thickness of the coated layer after drying became 50 $\mu$m, and dried to thereby prepare a sheet-like insect communication disturbing material having a supporting material (polyester film) on one side.

TEST EXAMPLE 4

The insect communication disturbing material prepared in Example 5 was cut into such a size that its coated area became 2 cm×2 cm and attached to a 1.5 m high branch of a plane tree to observe the behavior of *Hyphantria cunea* attracted thereby. Male adults attracted by the insect communication disturbing material contacted with it and immediately departed therefrom and were not attracted again during the action time of the day. In addition, other male adults were observed which approached the *Hyphantria cunea* males that had contacted with the insect communication disturbing material, attracted by the contacted males.

TEST EXAMPLE 5

The insect communication disturbing material prepared in Inventive Example 5 was cut into such a size that its coated area became 2 cm×2 cm, and the thus cut pieces were arranged on every other of 25 roadside trees (plane trees) in Sumida-ku, Tokyo, Japan. The arrangement was carried out three times on May 12, July 8 and August 20 before the emergence of adults, and the average number of nest webs of the next generation larvae was examined on June 15, August 19 and October 15 after respective emergences of adults. As a comparison, a non-treated plot was arranged and examined in the same manner.

As the result, average numbers of nest webs were 1.24 (first time), 1.54 (second time) and 0.25 (third time) in the non-treated plot and 1.09 (first time), 0.60 (second time) and 0 (third time) in the treated plot where the insect communication disturbing material was arranged, thus confirming that its insect communication disturbing effect becomes significant by its repeated arrangement.

Reference Example

A 24 mg portion of an ethylene/vinyl acetate copolymer was dissolved in 30 mg of toluene, and 6 mg of *Hyphantria cunea* pheromone was added to the resulting solution and uniformly dissolved.

The thus obtained solution was coated on a polyester film having a thickness of 75 $\mu$m in such an amount that thickness of the coated layer after drying became 50 $\mu$m and dried. A polyester film of 25 $\mu$m in thickness was adhered to the surface of the resulting pheromone-containing layer, thereby preparing a sandwich type insect communication disturbing material.

The thus prepared insect communication disturbing material was cut into a size of 2 cm×2 cm, and 10 of the thus cut pieces were arranged on 20 roadside trees (plane trees) in Ibaraki-shi, Osaka, Japan. The arrangement was carried out on July 16, and the average number of nest webs of the next generation larvae was examined on August 13 after the emergence of adults. As a comparison, a non-treated plot was arranged and examined in the same manner.

As the result, the average number of nest webs was 1.53 in the non-treated plot and 1.03 in the treated plot.

On the basis of the above results, it is evident that the insect communication disturbing effect of the insect communication disturbing material of the present invention is superior to that of the prior art non-exudation type disturbing material (Reference Example).

While the invention has been described in detail and with reference to specific embodiments thereof, it will be apparent to one skilled in the art that various changes and modifications can be made therein without departing from the spirit and scope thereof.

What is claimed is:

1. A method for disturbing insect communication which comprises attracting male adult insects to an insect communication disturbing material, thereby effecting contact of the male adults with said insect communication disturbing material and adhesion of a pheromone component to the body of the males, and subsequently allowing the contacted males to be free without capturing them, wherein the insect communication disturbing material comprises:

(A) a covering material having an exudable pheromone component included therein, and
   (B) an ultra-thin layer of about 0.1 to 10 $\mu$m in thickness of exuded pheromone component on at least one surface of said covering material, wherein the exuded pheromone component is transferable and adherable to insect pests which contact the insect communication disturbing material, and wherein the insect communication disturbing material does not contain insecticide.

2. The method for disturbing insect communication according to claim 1 wherein said pheromone component is impregnated into cotton, non-woven fabric, rubber, a porous polymer sheet or a hollow fiber membrane.

3. The method for disturbing insect communication according to claim 1, wherein said covering material has a shape of at least one form selected from a plastic sheet, a capsule, a tube and a hollow fiber membrane.

4. The method for disturbing insect communication according to claim 3, wherein said plastic sheet comprises two or more polyester resins having different glass transition temperatures.

5. The method for disturbing insect communication according to claim 1, wherein said covering material is selected from the group consisting of polyolefin, polysulfone, polyester, ethylene/vinyl acetate copolymer, polyamide, polystyrene and poly(meth)acrylate.

6. The method for disturbing insect communication according to claim 1, wherein said covering material is coated on one side of a supporting material.

* * * * *